(12) United States Patent
Pease

(10) Patent No.: US 9,027,609 B2
(45) Date of Patent: May 12, 2015

(54) ARGON GAS LEVEL CONTROLLER

(75) Inventor: John R. Pease, Ashford, CT (US)

(73) Assignee: United Technologies Corporation, Hartford, CT (US)

( * ) Notice: Subject to any disclaimer, the term of this patent is extended or adjusted under 35 U.S.C. 154(b) by 899 days.

(21) Appl. No.: 13/171,591

(22) Filed: Jun. 29, 2011

(65) Prior Publication Data

US 2012/0282416 A1 Nov. 8, 2012

Related U.S. Application Data

(60) Provisional application No. 61/481,802, filed on May 3, 2011.

(51) Int. Cl.
 *B65B 1/30* (2006.01)
 *G01N 33/00* (2006.01)
(52) U.S. Cl.
 CPC .................. *G01N 33/0062* (2013.01)
(58) Field of Classification Search
 CPC .................................................. G01N 33/0062
 USPC ........ 141/192, 198; 34/89, 201, 202; 426/418
 See application file for complete search history.

(56) References Cited

U.S. PATENT DOCUMENTS

| | | | | |
|---|---|---|---|---|
| 4,344,467 A | * | 8/1982 | Lahde | 141/66 |
| 5,799,495 A | * | 9/1998 | Gast et al. | 62/78 |
| 5,879,458 A | * | 3/1999 | Roberson et al. | 118/715 |
| 5,980,648 A | | 11/1999 | Adler | |
| 6,092,430 A | * | 7/2000 | Liston et al. | 73/863.81 |
| 6,488,986 B2 | | 12/2002 | Das et al. | |
| 7,156,960 B2 | | 1/2007 | Vanden Brande et al. | |
| 7,352,464 B2 | | 4/2008 | Chen et al. | |
| 7,878,112 B2 | * | 2/2011 | Naylor | 99/467 |
| 8,235,076 B2 | * | 8/2012 | Coignet et al. | 141/4 |
| 8,667,977 B1 | * | 3/2014 | McCaul et al. | 137/3 |
| 2010/0193067 A1 | | 8/2010 | Coignet et al. | |
| 2013/0059084 A1 | * | 3/2013 | Fairbourn et al. | 427/319 |

FOREIGN PATENT DOCUMENTS

EP 0467668 A1 1/1992

OTHER PUBLICATIONS

B.James Filla and Jane E. Callanan, Laboratory-scale controlled-atmosphere chamber for use with premium coal samples, 8127 Review of Scientific Instruments, 56 Apr. 1985, No. 4, Woodbury, New York, USA.

The European Search Report mailed Jun. 16, 2014 for European Application No. 12166236.5.

\* cited by examiner

*Primary Examiner* — Jason K Niesz
(74) *Attorney, Agent, or Firm* — Kinney & Lange, P.A.

(57) ABSTRACT

A controlled environment enclosure is disclosed. The enclosure has a tank with a lid, wherein the lid and tank are capable of creating a sealed enclosure. The enclosure also has a fluid filling inlet for introduction of a filling fluid into the tank, a fluid sensor for detecting a fluid other than the filling fluid, and a controller connected to the fluid sensor and the fluid filling inlet for selectively allowing the filling of the enclosure by the filling fluid through the fluid filling inlet.

3 Claims, 7 Drawing Sheets

ARGON GAS LEVEL CONTROLLER

CROSS-REFERENCE TO RELATED APPLICATION(S)

This application claims priority to U.S. Provisional Application No. 61/481,802, filed on May 3, 2011, and entitled "ARGON GAS LEVEL CONTROLLER", the disclosure of which is incorporated by reference in its entirety.

BACKGROUND

Many components for gas turbine engines require a coating to withstand the harsh environment in which the components operate. For example, turbine blades and vanes often contain a thermal barrier coating. The coating is applied in a multi-stage process. First, the raw metal part is cleaned. Second, a bond coating is administered to the components to bind the outer coating to the base metal alloy. Next, a plasma coat of an outer ceramic coating is applied to the bond coating. However, the process and facilities do not necessarily allow for the immediate succession of steps in the coating process. Often, there are hours or days between the cleaning of the part, the application of the bond coating, and the application of the final outer coating. During this time, the parts must be kept clean, and must not be allowed to oxidize.

The existing process in applying coatings to turbine components is to prevent oxidation on unfinished coated parts by submerging the parts in an unsealed purge tank, and continually flowing argon gas into the tank. However, the tank design with a continuous flow of argon is costly due to the continuous loss of argon gas because the tank is not sealed. Thus, there is a need to reduce the argon gas consumption regarding the use of the purge tank.

SUMMARY

A controlled environment enclosure is disclosed. The enclosure has a tank with accessible containment, and wherein the tank is capable of creating a sealed enclosure. The enclosure also has a fluid filling inlet in the tank, a fluid sensor for sensing presence of an unwanted fluid in the sealed enclosure, and a controller operatively connected to the fluid sensor for selectively allowing the filling of the enclosure through the fluid filling inlet in response to the fluid sensor sensing presence of the unwanted fluid.

Additionally, a method of coating a part can accomplished with the disclosed purge tank system that has the controlled environment enclosure. First, a part is cleaned. The part is stored in a controlled environment enclosure, wherein the enclosure controls a first parameter of the environment in the enclosure to prevent contamination of the cleaned part by sensing a second parameter in the tank and adjusting the environment within the tank. The environment in the enclosure is maintained by a control system. The part is removed from the enclosure, and a coating is applied to the part. This coating may be either a bond coating or a plasma coating that acts as a thermal barrier coating.

In another embodiment, a controlled environment system that has a fluid filling source is disclosed. The system also has a tank for accessible containment of components therein. A sensor mounted to the tank. Finally, the systems has a controller that causes filling fluid to be supplied from the fluid filling source to the tank in response to the sensor sensing presence of a fluid other than the filling fluid within a controlled environment region of the tank.

BRIEF DESCRIPTION OF THE DRAWINGS

These and other features, aspects, and advantages of the present invention will become apparent from the following description, appended claims, and the accompanying exemplary embodiments shown in the drawings, which are hereafter briefly described.

DETAILED DESCRIPTION

Figure 1:
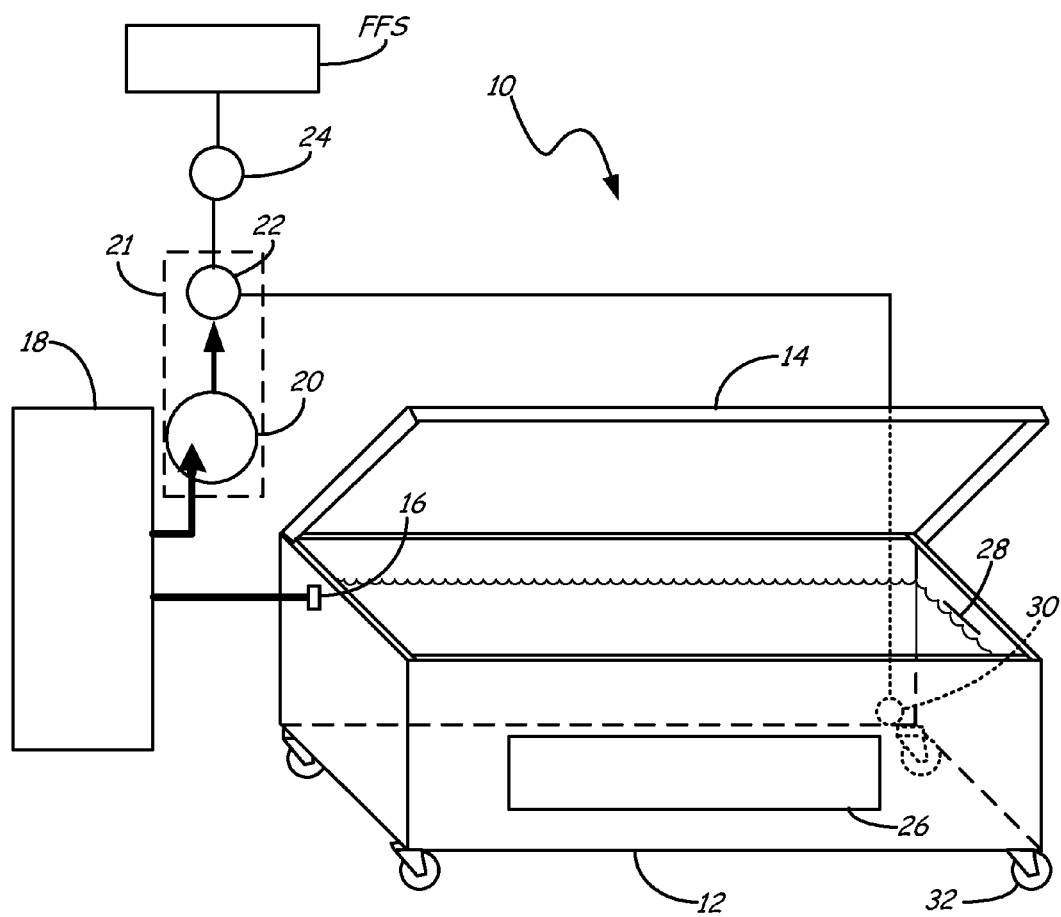
FIG. 1 is a schematic of a purge tank system with an argon gas level controller.

Efforts have been made throughout the drawings to use the same or similar reference numerals for the same or like components.

FIG. 1 is a perspective view of a purge tank system 10. The purge tank system provides a controlled environment enclosure for components, such as turbine blades and vanes that are awaiting a coating process. In one embodiment, the purge tank system prevents oxidation of the components. The purge tank system contains tank 12 with lid 14, sensor 16, controller 18, solenoid valve 21 having solenoid 20 and valve 22, and regulator 24. Tank 12 is constructed from aluminum or a similarly rigid material. Although illustrated as a rectangular prism, tank 12 may be of any geometry that allows for the placement and storage of the intended contents. In one embodiment, tank 12 contains window 26 that is a transparent area constructed from glass or polymer. Window 12 allows for visual monitoring of the components or part (not illustrated) contained within tank 12. Window 12 may be tinted to prevent light from contacting components or parts contained within tank 12.

Lid 14 is connected to tank 12 in a removeable or semi-removable arrangement, such as by hinges. Lid 14 is larger than the cross-sectional geometric area of the opening of tank 12 to form an enclosed area between lid 14 and tank 12. Lid 1 contains a rubber gasket that allows for creating a sealed structure with tank 12 when in the closed position. Lid 12 is constructed from the same or similar materials as tank 12, and in one embodiment, may contain a transparent area to allow for visual inspection of the contents of tank 12.

Tank 12 may also contain an indicator level 28, such as a painted mark, protrusion, or change in geometric cross-section, that indicates the desired full capacity for the fluid level within tank 12. A fluid inlet 30 is contained on the lower part of tank 12 that allows for the introduction of a filling fluid into tank 12. The filling fluid is a typically a noble gas that is heavier than air and oxygen, such as argon, and is supplied from fluid filling source FFS through regulator 24, valve 22, solenoid 20 and fluid inlet 30 to the interior of tank 12. Although illustrated as being on a wall, the inlet may also be on the floor of tank 12. It is preferable that fluid inlet 30 is below indicator level 28. Tank 12 also may contain castors 32 to allow for mobility of tank 12. This allows for the transport of components or parts within tank 12, which will keep the components within the fluid of tank 12 until just prior to removal for the coating process.

Sensor 16 is a gas sensor. In one embodiment, sensor 16 is an oxygen sensor, having an adjustable alarm range of 0-25%. Sensor 16 is located at the upper end of tank 12, and is meant to obtain readings from a fluid that is less dense that the filling fluid of tank, such as ambient air or oxygen. Thus, when the filling fluid drops to a level below the sensor, such as when ambient air is allowed to enter the tank upon opening the lid, the sensor will enter the alarm state and trigger action of the solenoid valve 21.

Figure 2:
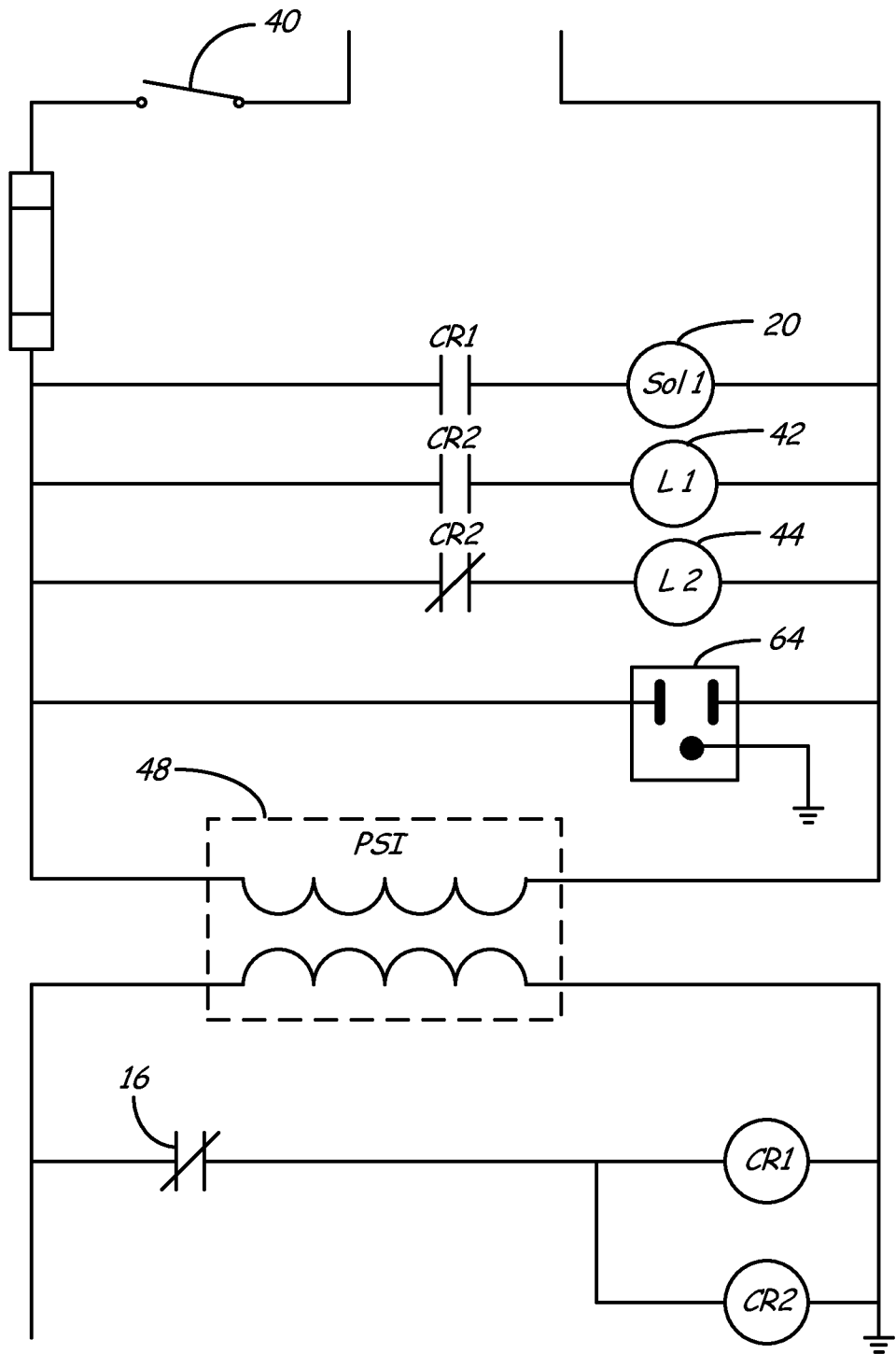
FIG. 2 is an electrical schematic of the argon gas level controller.
Figure 3:
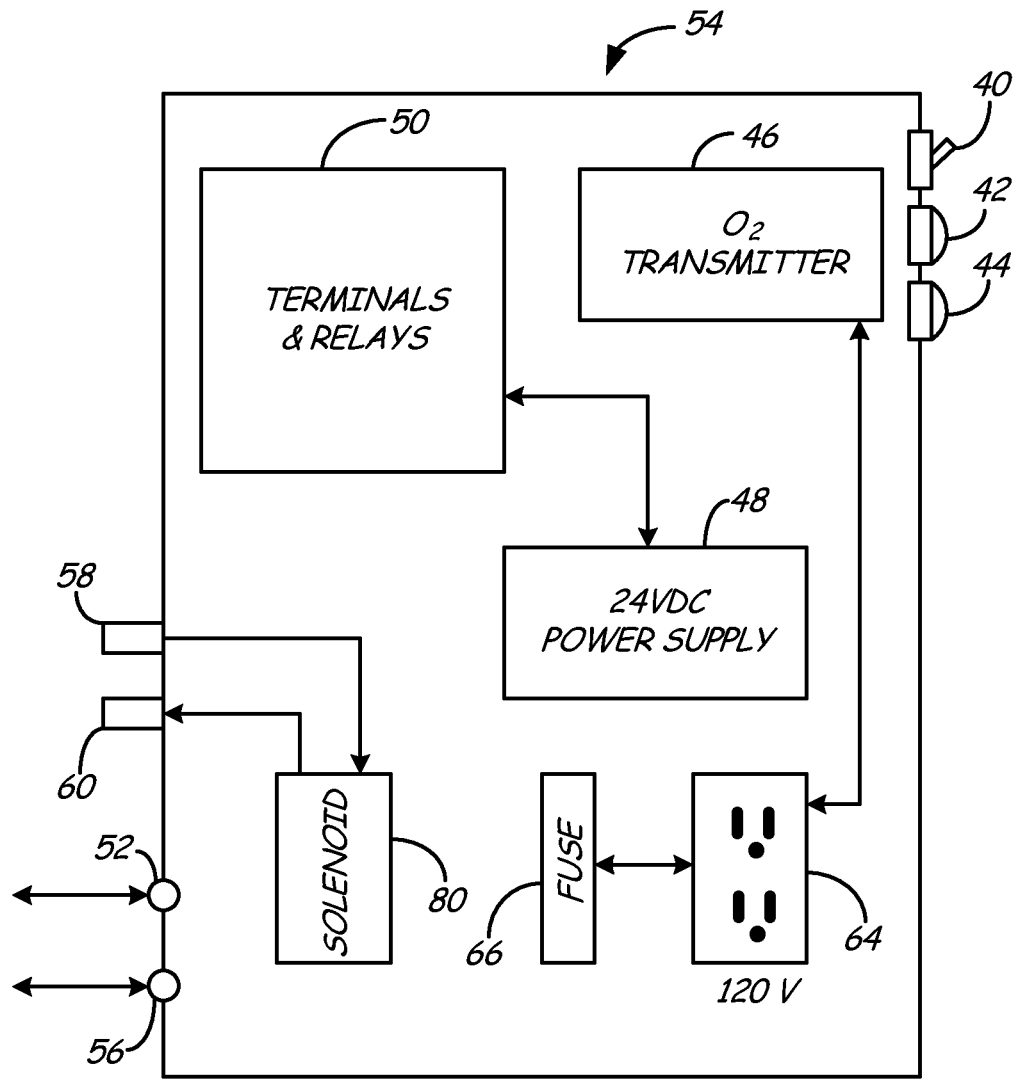
FIG. 3 is a schematic of the argon gas level controller hardware.
Figure 4:
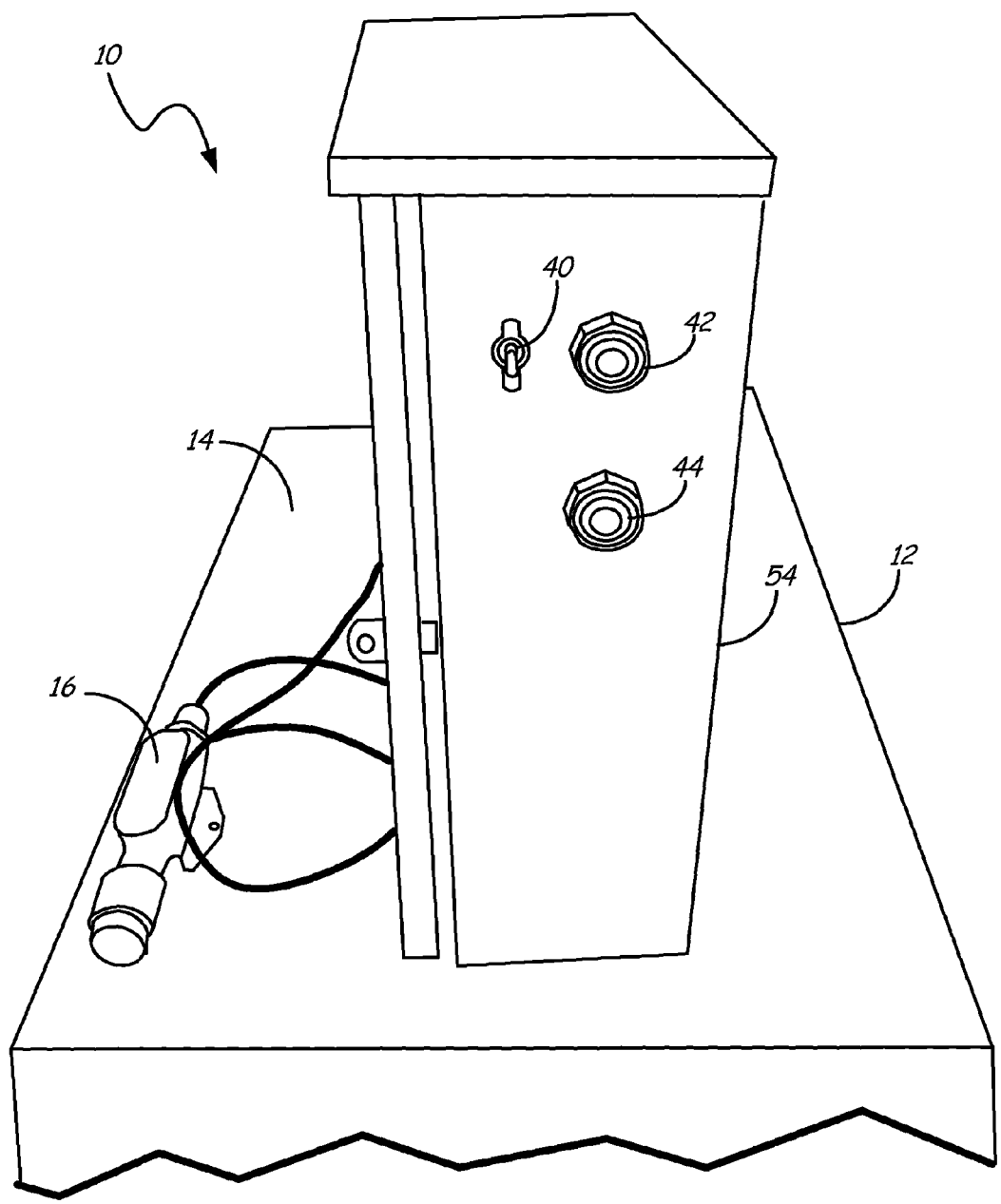
FIG. 4 is a perspective view one embodiment of the argon gas level controller.
Figure 5:
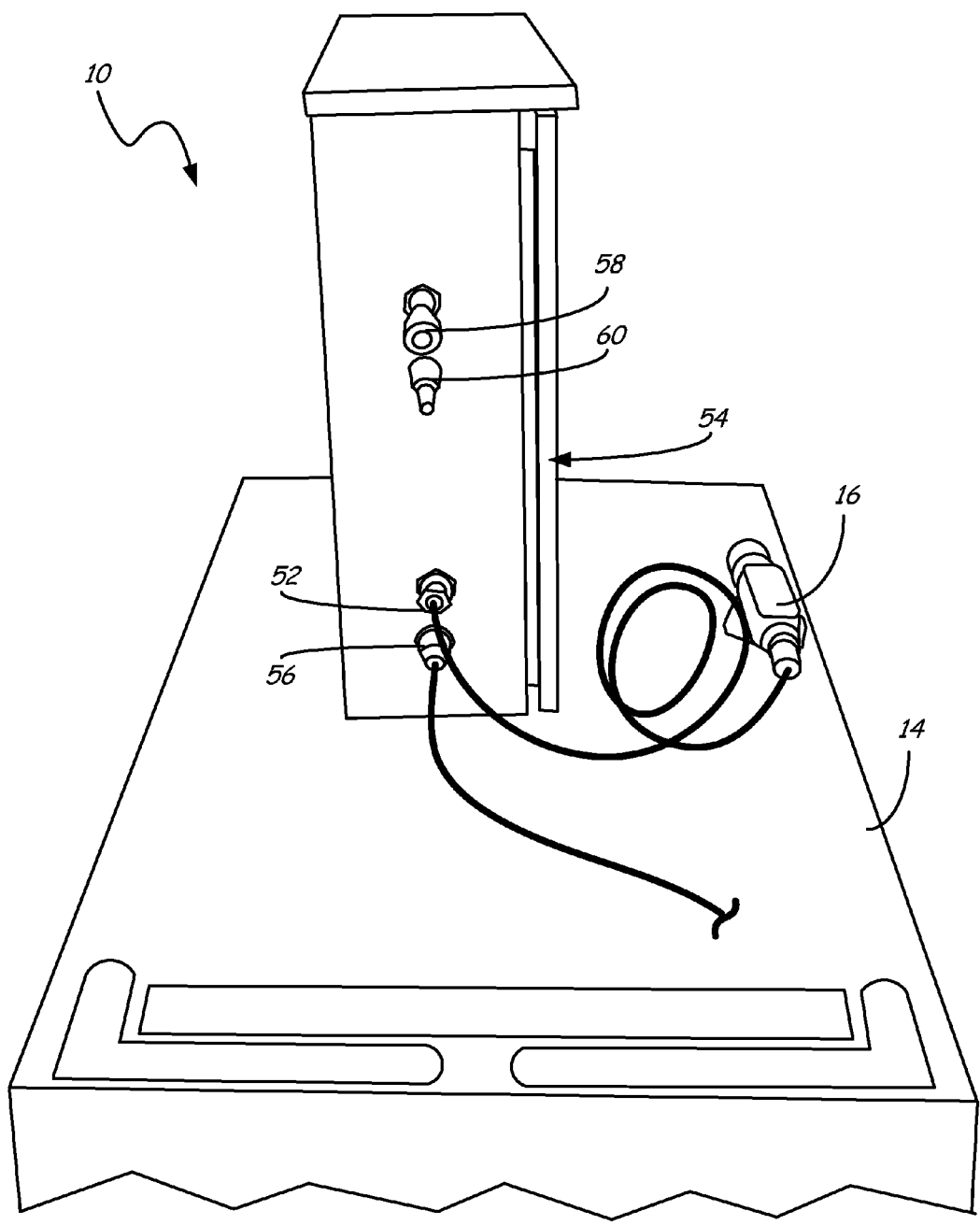
FIG. 5 is another perspective view of the argon gas level controller.
Figure 6:
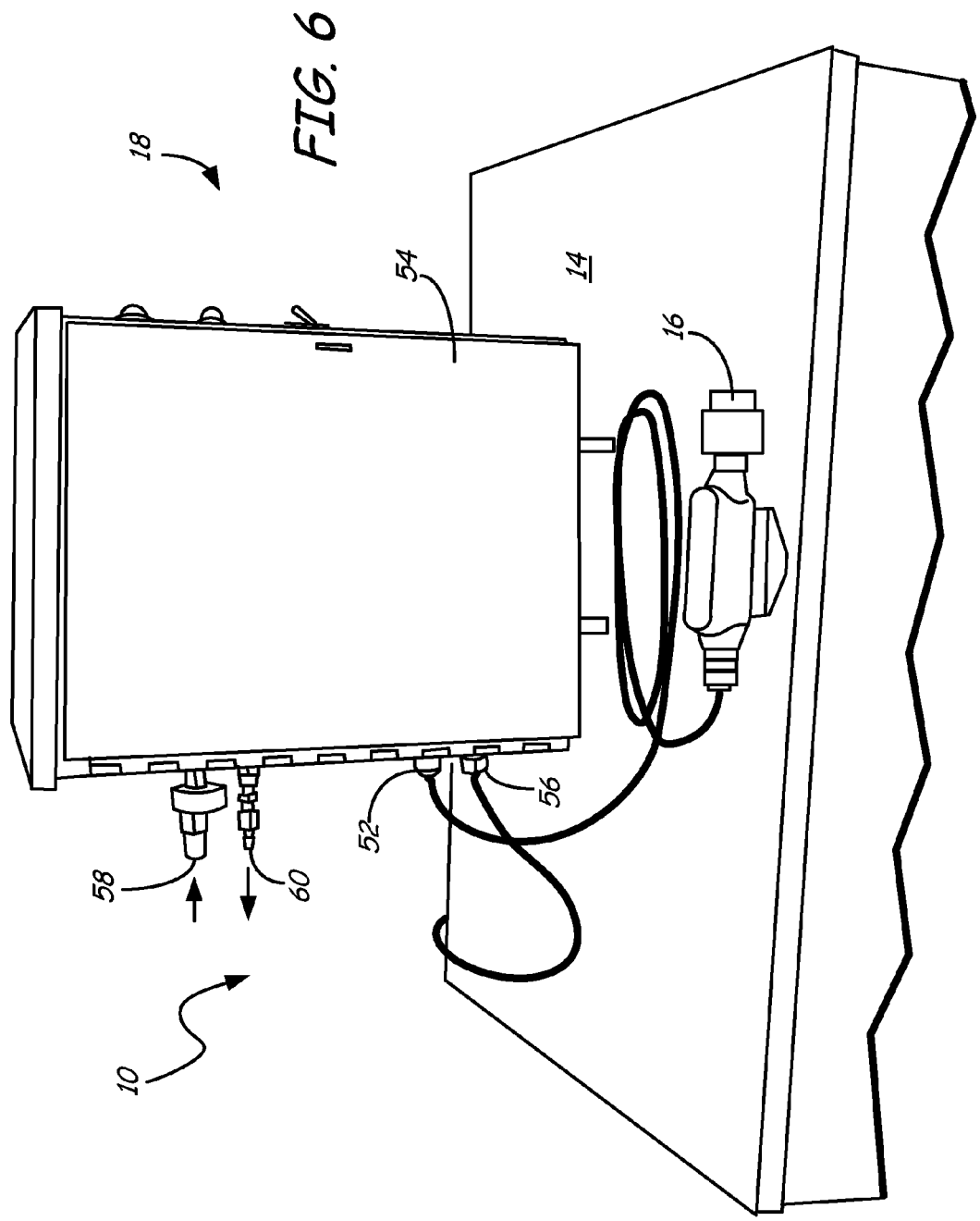
FIG. 6 is a front perspective of the argon gas level controller.
Figure 7:
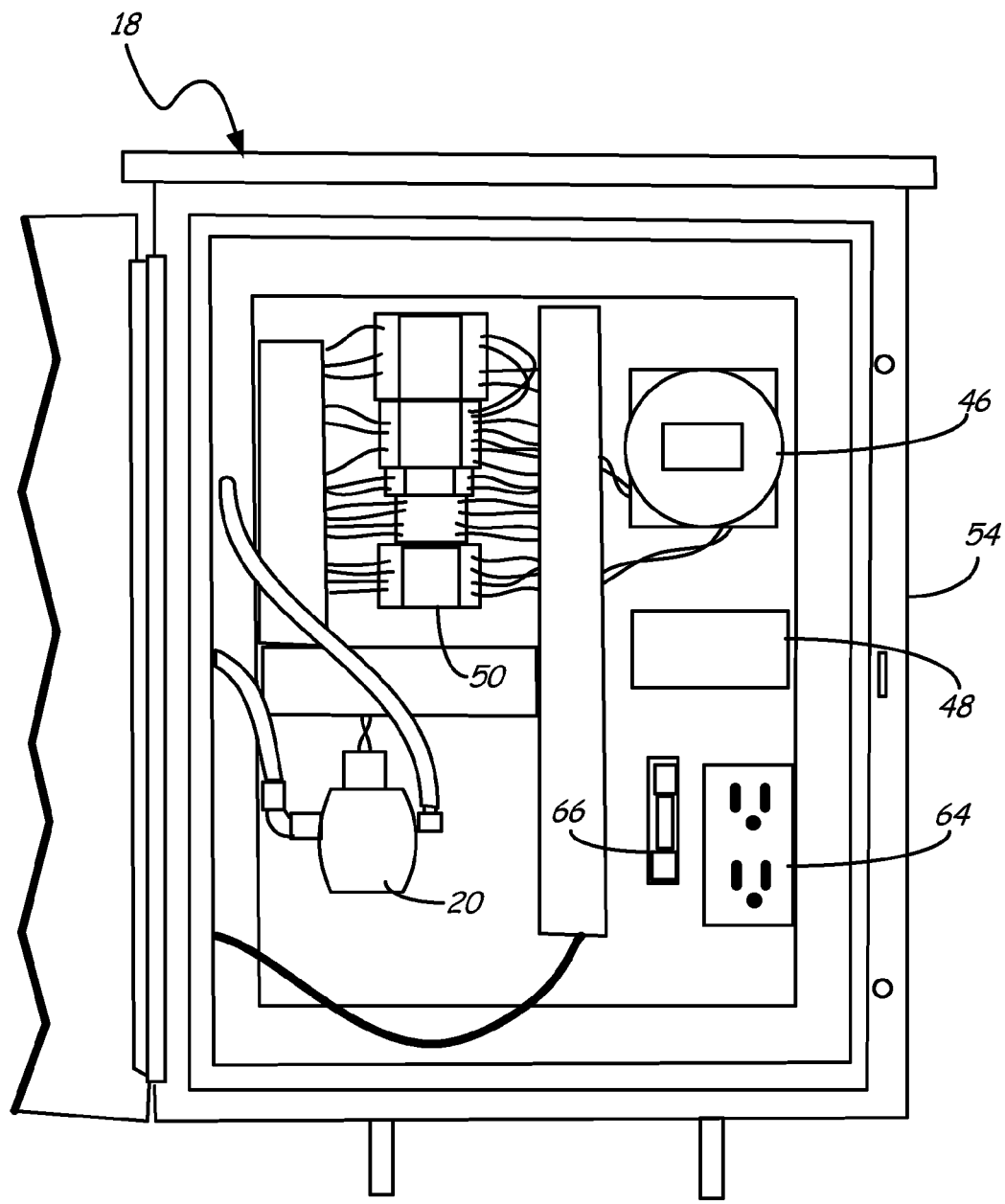
FIG. 7 is a front view of the argon gas level controller with the front cover removed.

FIG. 2 is an electrical schematic of a fluid level controller 18, and FIG. 3 is a schematic of the fluid level controller hardware. FIGS. 4-7 are various perspective views the fluid level controller 18 for purge tank system 10. Fluid level controller 18 has switch 40, fluid level indicator 42, fluid filling indicator 44, sensor transmitter 46, power supply 48, terminals and relays 50, and solenoid 20. FIG. 2 illustrates one embodiment for the electrical connections between controller 18 components, while FIGS. 3-7 illustrated the hardware components associated with controller 18. The components are contained within panel box 54, which may be a NEMA class 1 enclosure. Box 54 contains power inlet 56 for allowing connection to a 120 VAC standard wall socket. An inlet 52 for running the electrical wiring to the sensor 16 is adjacent power inlet 56. Box 54 also contains filling fluid inlet 58 and fluid inlet 60.

When the tank 12 is at a desired fill level, solenoid 52 is closed, and fluid level indicator 42 is activated. When the level of the filling fluid drops below the desired level, i.e., when sensor 16 enters the alarm state, solenoid 52 will be opened and fluid filling indicator 44 will be activated. In one embodiment, fluid level indicator 42 and fluid filling indicator 44 are lights of differing colors, such as green and red respectively, that illuminate when activated. In other embodiments, fluid level indicator 42 and fluid filling indicator 44 may be different audible noises, gauges, or spring-loaded buttons.

Power supply 48 is a 120 VAC to 24 DC, or similar reducer known to those of skill in the art. The output of power supply 48 matches that of the other components, including the terminals and relays 50, which are also known in the art. Box 54 also contains a 120 VAC link or outlet socket 64, and fuse 66 to protect the components from electrical fluctuations.

Solenoid valve 21 is contained within box 54, and contains valve 22 and solenoid 20. Filling inlet 60 is in communication with valve 22, which is controlled by solenoid 20. Valve 22 is a ball valve or similar valve known to those of skill in the art. A second end of valve 22 is connected to a filling tank or supply of fluid such as fluid filling source via filling fluid inlet 58. The filling tank may contain regulator 24 to control the flow of the filling fluid from fluid filling source FFS to tank 12.

Purge tank systems 10 monitors the level of a fluid in tank 12 at a certain level (full) and energizes and de-energizes solenoid 20, which activates valve 22, to maintain that level of fluid. The fluid is typically a heavy noble gas, such as argon. In previous systems, the tanks were not sealed, and the filling fluid (argon) was continuously flowed into the tank. The continuous flow was necessary to assure no ambient air was in the tank, which would allow for the oxidation of the components or parts contained therein.

In operation, sensor 16 is a normally closed contact (see FIG. 2). Upon opening the contact, coil CR1 is energized, thus closing the normally open contact for solenoid 20, which will close valve 22. In the normally closed state of sensor 16, CR1 is not energized, and the solenoid is open, and thus valve 22 is open. Similarly, a charging of coil CR2 will close the contacts for fluid level indicator 42 and open the contact for fluid filling indicator 44, and thus switching which indicator is powered.

Tank 12 with a sealed lid 14 prevents ambient air flow and currents from "pushing" out the argon gas. Only when an operator opens the cover to place or remove parts from the tank will some argon in the tank gets replaced by ambient air. As argon is heavier then air, it behaves like water in a bathtub. When the sensor detects the level is below full, the sensor triggers the controller to turn on a relay to "denergize" the solenoid and allow filling gas to fill the tank. Sensor 16 is set to 5% alarm trip but is adjustable down to 1%. The system uses a normally open solenoid that is held closed when energized so that in the event of loss of power, the "purge tank" reverts back to the operation of the prior art system with constant flow to maintain the level in the tank and protect the parts with a constant flow of argon.

The indicators, such as lights, on the unit to let operators know when the system is filling and when the desired level has been reached and maintained. After the desired level has been reached, the lid may be closed. Alternately, the seal in lid 14 may allow for the expulsion of the lighter gases during the filling of tank 12, but keep out ambient air from the enclosure created by tank 12 and lid 14. In another embodiment, an outlet is provided either adjacent to or in the lid. The outlet is controlled to selectively open when tank 12 if being filled, and close once the desired level has been reached. In one embodiment, purge tank system 10 also has a non-resetable hour meter or similarly device that can accurately track usage of the filling fluid. The system flows argon to maintain the tank level between 54 and 60 minutes daily, down from the continuous flow of the prior art system. This time may increase or decrease depending upon the time the tank is open for the placement and retrieval of components ands parts stored therein. When calculating the amount of argon gas saved by the use of the disclosed system, annual savings of over thirty-six thousand dollars are attributable to the purge tank system 10 from the prior art systems described.

A method of coating a part can accomplished with the disclosed purge tank system. First, a part is cleaned. The part is stored in a controlled environment enclosure, wherein the enclosure controls a fluid level of a filling fluid in the enclosure with a control system to prevent contamination of the cleaned part by sensing the level of a second fluid and adjusting the amount of filling fluid within the tank. The level of the filling fluid is maintained in the enclosure by the control system. The part is removed from the enclosure, and a coating is applied to the part. This coating may be either a bond coating or a plasma coating that acts as a thermal barrier coating.

Additionally, the part in the controlled environment enclosure may be stored a second time after application of a first stage of the coating process. The component from the controlled environment enclosure, a second stage coating is applied to the component. The part may be moved in the controlled environment enclosure between coating stages, or from the cleaning area to the first stage coating application area.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s)

disclosed, but that the invention will include all embodiments falling within the scope of the appended claims.

The invention claimed is:

1. A controlled environment system comprising:
   a tank including a base, a sidewall extending from the base, and an access lid configured to connect to the sidewall, wherein the lid, base, and sidewalls form a sealed enclosure that prohibits the escape of gases contained therein;
   a level indicator positioned on the sidewall at a first height above the base;
   an oxygen sensor positioned at least equal to the first height;
   an inlet located at a second height that is less than the first height, wherein the inlet is configured to receive a fluid for filling the tank, wherein the fluid has a greater molecular weight than that of ambient air;
   a fluid filling system connected to the inlet, the fluid filling system configured to contain the fluid with a greater molecular weight than that of ambient air, the fluid filling system comprising:
      a controller for selectively allowing the filling of the enclosure by the fluid through the inlet in response to the oxygen sensor sensing presence of the ambient air.

2. The system of claim 1 wherein the fluid filling system further comprises:
   a fluid reservoir;
   a solenoid valve; and
   a fluid regulator.

3. The system of claim 1 wherein the access lid includes a gasket.

* * * * *